United States Patent [19]

Engelmann

[11] Patent Number: 4,738,823
[45] Date of Patent: Apr. 19, 1988

[54] TEST STRIP WITH ADJUSTABLE SAMPLE ABSORPTION CAPACITY

[75] Inventor: Helmut Engelmann, Leverkusen, Fed. Rep. of Germany

[73] Assignee: Miles Laboratories, Inc., Elkhart, Ind.

[21] Appl. No.: 893,986

[22] Filed: Aug. 7, 1986

[30] Foreign Application Priority Data

Aug. 30, 1985 [DE] Fed. Rep. of Germany ....... 3530993

[51] Int. Cl.⁴ ............................................ G01N 31/22
[52] U.S. Cl. ........................................ 422/56; 422/58
[58] Field of Search ................. 422/56, 58; 435/805; 436/170; 264/1.7; 156/73.1

[56] References Cited

U.S. PATENT DOCUMENTS

| | | | |
|---|---|---|---|
| 2,918,893 | 12/1959 | Norton | 422/56 X |
| 3,067,015 | 12/1962 | Lawdermilt | 422/56 |
| 3,809,617 | 5/1974 | Schmitt | 422/56 X |
| 4,178,153 | 12/1979 | Sodickson | 422/58 X |
| 4,181,500 | 1/1980 | Cowsar et al. | 422/56 X |
| 4,199,550 | 4/1980 | Wielinger et al. | 422/58 |
| 4,254,083 | 3/1981 | Columbus | 422/56 X |
| 4,323,536 | 4/1982 | Columbus | 422/58 X |
| 4,631,174 | 12/1986 | Kondo | 422/56 |

*Primary Examiner*—David L. Lacey
*Assistant Examiner*—Jill Johnston
*Attorney, Agent, or Firm*—Roger N. Coe

[57] ABSTRACT

A test strip with a sample absorption capacity which can be preselected comprises a support member capable of supporting along at least two edges a reagent strip in which the support member also has absorbent material positioned to remove excess sample applied to the reagent strip. In a preferred embodiment an intermediate layer is also supported by the support member and positioned above the reagent strip. The intermediate layer removes components of the sample which would otherwise interfere with the analysis being made in the reagent strip. In a further embodiment of the invention a cover is applied to the support member, wherein the cover contains an opening for introduction of sample material.

4 Claims, 1 Drawing Sheet

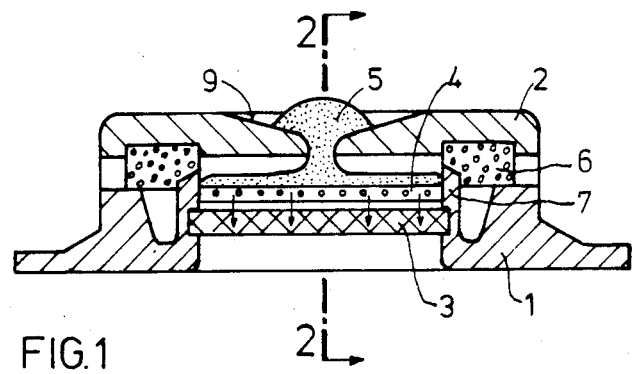
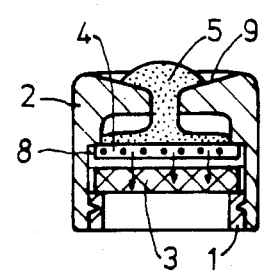
FIG. 1  FIG. 2
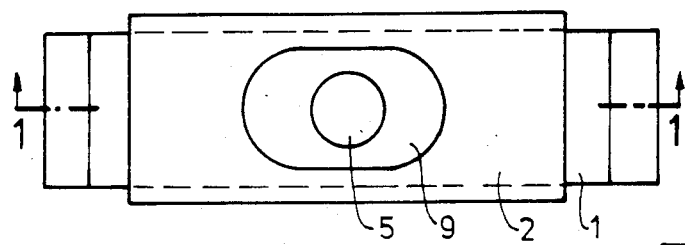
FIG. 3
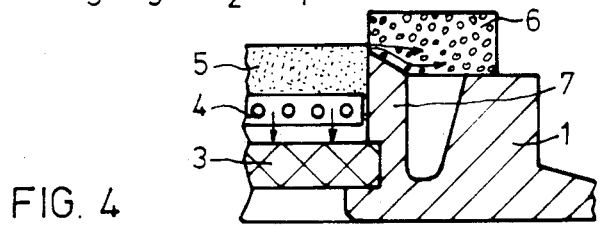
FIG. 4
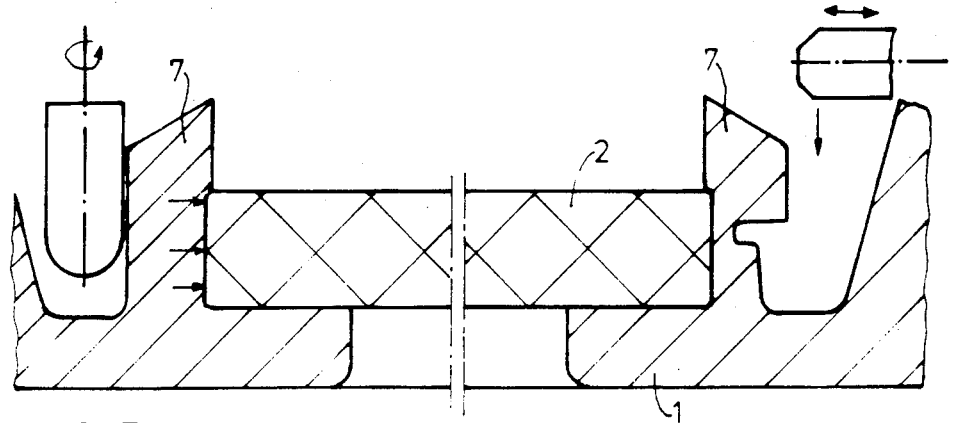
FIG. 5

TEST STRIP WITH ADJUSTABLE SAMPLE ABSORPTION CAPACITY

The invention relates to a test strip with a sample absorption capacity which can be specified and a process for its production. In this test strip, the reagent strip (3) is fixed in a depression of a support member or carrier (1). The size of this depression determines the volume of sample which can be absorbed. Excess sample liquid is taken up by an absorbent material (6) on the edge of the depression or gap.

The importance of test strips as analytical agents, especially in the field of clinical chemistry, has increased more and more in the last few years. One field of use, for example, involves monitoring the blood sugar level by diabetics themselves. A similarly important field of application is the use of such test strips by primary care physicians as a rapid diagnostic aid. Metering identical amounts of sample is a great problem. If the test strips are used for qualitative investigations, the volume of sample is of no significance. However, if the test strips are used for quantitative analyses, exact metering of the sample is necessary. By their nature, however, reagent strips themselves are not suitable for absorbing an exact and reproducible amount of sample liquid. The sample is therefore usually metered with the aid of pipettes. This can be carried out reproducibly and with the required accuracy only by specialized personnel in laboratories, but not in self-diagnosis applications.

It is also frequently necessary to wipe the reagent strips in order to remove constituents in the sample liquid which interfere with the measurement, such as, for example, red blood corpuscles in the analysis of whole blood. As a result of this wiping process, there is the possibility that sample liquid will be pressed into or sucked out of the reagent strip.

The present invention was based on the object of providing a test strip which has a sample absorption capacity which can be specified, that is to say a test strip in which a precisely predetermined amount of sample liquid gets into the reagent strip. Excess sample is automatically removed.

Other and further objects, advantages, and features of the invention will be apparent to those skilled in the art from the following detailed description thereof, taken in conjunction with the accompanying drawings, in which:

FIG. 1 is a schematic view, in cross-section, of apparatus in accordance with the present invention taken along lines 1—1 of FIG. 3;

FIG. 2 is a schematic view, in cross-section, of the portion of FIG. 1 taken along lines 2—2;

FIG. 3 is a plan view of test apparatus in accordance with the present invention;

FIG. 4 illustrates a segment from FIG. 1, in enlarged cross-section; and

FIG. 5 illustrates, in greatly enlarged cross-section, a way of forming the test device of FIG. 1.

The invention relates to a test strip with a sample absorption capacity which can be specified, in which the reagent strip (3) is fixed in a depression or gap of the carrier (1), the size of the depression determining the volume of sample which can be absorbed and the depression having on its edge an absorbent material (6), which serves to take up excess sample liquid. In this arrangement the carrier (1) has the shape or profile having one or more depressions for accommodating the reagent strip (3).

Suitable carriers are all the materials known for this purpose, such as, for example, hard papers, metals or plastics. Particularly suitable materials are thermoplastics, such as, for example, polyethylene, polypropylene, polyamides or polyesters, which can be extruded to produce the desired carrier profile. Carrier profiles can, however, also be produced by combining several components, which are then bonded to one another, for example, by gluing.

The reagent strip (3) can consist of any material customary and known for each particular purpose, such as, for example, paper, gelatin, cellulose or plastic. Reagent strip (3) is understood here as a matrix material which contains particular reaction substances necessary for the analysis, such as, for example, enzymes, substrates, co-enzymes and indicators. The reagent strip can consist of one (single layer) or several (multilayer) layers.

The absorbent material (6) on the edge of the depression, which serves to take up excess sample, can be, for example, paper or fabric. However, plastics which are capable of absorbing liquids, in particular water, are also suitable. The ability to absorb liquid can be considerably influenced by pretreating the absorbent material, for example, by wetting agents or the introduction of functional groups.

Test strips can furthermore be provided with a cover (2) in which there is an opening for application of the sample (5). Between this application point for the sample (5) and the reagent strip is preferably an intermediate layer (4) which serves to remove undesired constituents from the sample (5). This intermediate layer (4) can have, for example, filtration properties for removing blood cells. The undesired constituents of the sample (5) can, however, also be bonded to this intermediate layer (4) by ador absorption. This can be effected, for example, by functional groups (ion exchangers) or also antibodies.

Undesired constituents of the samples are to be understood as substances which are capable of influencing the desired detection reaction or the measurement of this reaction. The intermediate layer (4) can also improve the distribution of the sample (5) on the reagent strip (spreading layer).

An essential feature in the production of the test strip according to the invention is the carrier (1), which must have the shape or profile with one or more depressions. Such a profile can be produced, for example, by extruding or by combining and subsequently bonding several components. The reagent strip (3) is laid and fixed in the depression. The absorbent material (6) is applied and likewise fixed on edges of the depression. Fixing can be effected either with the aid of adhesives or by shaping the carrier. Shaping is effected by heat and/or pressure. By shaping the carrier, a type of "press fit" is produced, which holds the reagent strip (3) and/or the absorbent material (6) firmly on the carrier (1). Introduction of the reagent strip by pouring is also suitable. If the carrier matrix for the reagent strip consists, for example, of plastic, this can be introduced into the depression in the form of a solution, in the molten state or as monomers. Hardening is then effected by drying, cooling or polymerization. In the use of, for example, gelatin as the carrier matrix, it is thus to be regarded as advantageous to introduce this into the depression in the molten state. The reagents necessary for the analysis can be added to the carrier matrix before pouring into the depression, or can be introduced by an impregnation operation after hardening of the carrier matrix.

A test strip according to the invention is shown and a process for its production is described below by way of example in FIGS. 1 to 5.

FIG. 1 shows a longitudinal section of a test strip. A reagent strip (3) is laid and fixed in the carrier support or profile (1). Above the reagent strip is an intermediate layer (4), which can be used for holding back undersired constituents of the sample (5). It also ensures uniform distribution of the sample (5). In this example, this intermediate layer (4) is bonded firmly to the cover (2) via the connecting point (8), as shown in FIG. 2. After the sample (5) has been applied to the test strip and has become distributed, the cover (2) with the attached intermediate layer (4) can be removed, together with the undesired constituents of the sample (5). The test strip can then be subjected to measurement. FIG. 2 shows a cross-section of the test strip. FIG. 3 shows a plan view of the test strip with the cover (2) in which there is an opening for application of the sample. The depression (9) around the opening facilitates the guiding of the sample (5) towards this opening.

FIG. 4 shows a section from FIG. 1 in which the arrangement of reagent strip (3), intermediate layer (4) and absorbent material (6), in relation to one another, are shown again.

FIG. 5 shows a greatly enlarged view, by way of example, of the fixing of the pressed-in reagent strip, which is effected by means of heated pressure rollers by plastic shaping (left) or, preferably, by ultrasonic shaping (right), the ultrasonic booster effecting shaping of the carrier (1) in the region of the web (7) without contact, and thus producing a firm connection.

In FIG. 5 (as also in FIG. 1, FIG. 2 and FIG. 4), the carrier has an opening below the reagent strip. Measurement can be effected through this opening (for example reflection, emission of light or fluorescence). If transparent reagent strips are used, measurement can also be effected with an absorption photometer. Such an opening can be dispensed, however, with transparent carriers. As already mentioned above, the test strip can be introduced into the depression by pouring, which makes separate fixing or attachment of the reagent strip to the carrier unnecessary.

Obviously, many other modifications and variations of the invention as hereinbefore set forth can be made without departing from the spirit and scope thereof.

What is claimed is:

1. A device for the quantitative analysis of liquid sample, which test device comprises:
   a support member having a depression therein,
   a reagent matrix positioned in said depression, and
   liquid absorbent material positioned at the edges of said depression to absorb excess liquid sample, thereby providing a reproducible sample volume.

2. The test device of claim 1 wherein the test device further comprises a cover over the depression in the support member and wherein the cover has an opening for the introduction of a sample.

3. The test device of claim 1 which further comprises an intermediate layer for removing undesired constituents from a liquid sample, said intermediate layer being liquid permeable and positioned in the depression above the reagent matrix.

4. The test device according to claim 1 in which the absorbent material is paper, fabric or plastic which absorbs excess sample.

* * * * *